US005549912A

United States Patent [19]
Oshlack et al.

[11] Patent Number: 5,549,912
[45] Date of Patent: *Aug. 27, 1996

[54] CONTROLLED RELEASE OXYCODONE COMPOSITIONS

[75] Inventors: Benjamin Oshlack, New York, N.Y.; Mark Chasin, Manalpan, N.J.; John J. Minogue, Mount Vernon, N.Y.; Robert F. Kaiko, Weston, Conn.

[73] Assignee: Euro-Celtique, S.A., Luxembourg, Luxembourg

[*] Notice: The term of this patent shall not extend beyond the expiration date of Pat. No. 5,266,331.

[21] Appl. No.: 81,302

[22] PCT Filed: Nov. 25, 1992

[86] PCT No.: PCT/US92/10146

§ 371 Date: Jun. 18, 1993

§ 102(e) Date: Jun. 18, 1993

[87] PCT Pub. No.: WO93/10765

PCT Pub. Date: Jun. 10, 1993

Related U.S. Application Data

[63] Continuation-in-part of Ser. No. 800,549, Nov. 27, 1991, Pat. No. 5,266,331.

[51] Int. Cl.⁶ ............................... A61K 9/22; A61K 9/26
[52] U.S. Cl. ...................... 424/468; 424/469; 424/470; 424/486; 424/487; 424/488; 424/494; 424/496; 424/497; 424/498; 424/501; 424/502; 424/495
[58] Field of Search ................ 424/486, 468–470, 424/487–88, 494, 496–498, 464–469

[56] References Cited

U.S. PATENT DOCUMENTS

| | | | |
|---|---|---|---|
| 4,861,598 | 8/1989 | Oshlack | 424/470 |
| 4,990,341 | 2/1991 | Goldie et al. | 424/484 |

Primary Examiner—Edward J. Webman
Attorney, Agent, or Firm—Steinberg, Raskin & Davidson, P.C.

[57] ABSTRACT

A method for substantially reducing the range in daily dosages required to control pain in approximately 90% of patients is disclosed whereby an oral solid controlled release dosage formulation having from about 10 to about 40 mg of oxycodone or a salt thereof is administered to a patient. The formulation provides a mean maximum plasma concentration of oxycodone from about 6 to about 60 ng/ml from a mean of about 2 to about 4.5 hours after administration, and a mean minimum plasma concentration from about 3 to about 30 ng/ml from about 10 to about 14 hours after repeated "q12h" (i.e., every 12 hour) administration through steady-state conditions. Another embodiment is directed to a method for substantially reducing the range in daily dosages required to control pain in substantially all patients by administering an oral solid controlled release dosage formulation comprising up to about 160 mg of oxycodone or a salt thereof, such that a mean maximum plasma concentration of oxycodone up to about 240 ng/ml from a mean of up to about 2 to about 4.5 hours after administration, and a mean minimum plasma concentration up to about 120 ng/ml from about 10 to about 14 hours after repeated "q12h" (i.e., every 12 hour) administration through steady-state conditions are achieved. Controlled release oxycodone formulations for achieving the above are also disclosed.

9 Claims, 5 Drawing Sheets

CONTROLLED RELEASE OXYCODONE COMPOSITIONS

This application is a continuation-in-part of U.S. patent application Ser. No. 07/800,549, filed Nov. 27, 1991, now U.S. Pat. No. 5,266,331.

BACKGROUND OF THE INVENTION

Surveys of daily dosages of opioid analgesics required to control pain suggest that an approximately eight-fold range in daily dosages is required to control pain in approximately 90% of patients. This extraordinary wide range in the appropriate dosage makes the titration process particularly time consuming and resource consuming, as well as leaving the patient without acceptable pain control for an unacceptably long duration.

In the management of pain with opioid analgesics, it has been commonly observed and reported that there is considerable inter-individual variation in the response to a given dose of a given drug, and, therefore, considerable variability among patients in the dosage of opioid analgesic required to control pain without unacceptable side effects. This necessitates considerable effort on the part of clinicians in establishing the appropriate dose in an individual patient through the time consuming process of titration, which requires careful assessment of both therapeutic and side effects and dosage adjustments over a period of days and sometimes longer before the appropriate dosage is determined. The American Pain Society's 3rd Edition of Principles of Analgesic Use in the Treatment of Acute Pain and Cancer Pain explains that one should "be aware that the optimal analgesic dose varies widely among patients. Studies have shown that in all age groups, there is enormous variability in doses of opioids required to provide relief, even among opioid naive patients with identical surgical lesions . . . . This great variability underscores the need to write analgesic orders that include provision for supplementary doses, and to use intravenous boluses and infusions to provide rapid relief of severe pain . . . . Give each analgesic an adequate trial by dose titration . . . before switching to another drug."

An opioid analgesic treatment which acceptably controls pain over a substantially narrower daily dosage range would, therefore, substantially improve the efficiency and quality of pain management.

It has previously been known in the art that controlled release compositions of opioid analgesics such as morphine, hydromorphone or salts thereof could be prepared in a suitable matrix. For example, U.S. Pat. No. 4,990,341 (Goldie), also assigned to the assignee of the present invention, describes hydromorphone compositions wherein the dissolution rate in vitro of the dosage form, when measured by the USP Paddle Method at 100 rpm in 900 ml aqueous buffer (pH between 1.6 and 7.2) at 37° C., is between 12.5 and 42.5% (by wt) hydromorphone released after 1 hour, between 25 and 55% (by wt) released after 2 hours, between 45 and 75% (by wt) released after 4 hours and between 55 and 85% (by wt) released after 6 hours.

SUMMARY OF THE INVENTION

It is an object of the present invention to provide a method for substantially improving the efficiency and quality of pain management.

It is another object of the present invention to provide an opioid analgesic formulation which substantially improves the efficiency and quality of pain management.

It is another object of the present invention to provide a method and formulation(s) which substantially reduce the approximately eight-fold range in daily dosages required to control pain in approximately 90% of patients.

It is another object of the present invention to provide a method and formulation(s) which substantially reduce the variability in daily dosages and formulation requirements necessary to control pain in substantially all patients.

It is yet another object of the present invention to provide a method for substantially reducing the time and resources need to titrate patients requiring pain relief on opioid analgesics.

It is yet another object of the present invention to provide controlled release opioid formulations which have substantially less inter-individual variation with regard to the dose of opioid analgesic required to control pain without unacceptable side effects.

The above objects and others are attained by virtue of the present invention, which is related to a solid controlled release oral dosage form, the dosage form comprising from about 10 to about 40 mg of oxycodone or a salt thereof in a matrix wherein the dissolution rate in vitro of the dosage form, when measured by the USP Paddle Method at 100 rpm in 900 ml aqueous buffer (pH between 1.6 and 7.2) at 37° C. is between 12.5 and 42.5% (by wt) oxycodone released after 1 hour, between 25 and 56% (by wt) oxycodone released after 2 hours, between 45 and 75% (by wt) oxycodone released after 4 hours and between 55 and 85% (by wt) oxycodone released after 6 hours, the in vitro release rate being substantially independent of pH, such that the peak plasma level of oxycodone obtained in vivo occurs between 2 and 4.5 hours after administration of the dosage form.

USP Paddle Method is the Paddle Method described, e.g., in U.S. Pharmacopoeia XXII (1990).

In the present specification, "substantially independent of pH" means that the difference, at any given time, between the amount of oxycodone released at, e.g., pH 1.6, and the amount released at any other pH, e.g., pH 7.2 (when measured in vitro using the USP Paddle Method at 100 rpm in 900 ml aqueous buffer), is 10% (by weight) or less. The amounts released being, in all cases, a mean of at least three experiments.

The present invention is further related to a method for substantially reducing the range in daily dosages required to control pain in approximately 90% of patients, comprising administering an oral solid controlled release dosage formulation comprising from about 10 to about 40 mg of oxycodone or a salt thereof, said formulation providing a mean maximum plasma concentration of oxycodone from about 6 to about 60 ng/ml from a mean of about 2 to about 4.5 hours after administration, and a mean minimum plasma concentration from about 3 to about 30 ng/ml from a mean of about 10 to about 14 hours after repeated "q12h" (i.e., every 12 hour) administration through steady-state conditions.

The present invention is further related to a method for substantially reducing the range in daily dosages required to control pain in substantially all patients, comprising administering an oral solid controlled release dosage formulation comprising up to about 160 mg of oxycodone or a salt thereof, said formulation providing a mean maximum plasma concentration of oxycodone up to about 240 ng/ml from a mean of up to about 2 to about 4.5 hours after administration, and a mean minimum plasma concentration up to about 120 ng/ml from a mean of about 10 to about 14 hours after repeated "q12h" (i.e., every 12 hour) administration through steady-state conditions.

The present invention is further related to controlled release oxycodone formulations comprising from about 10 to about 40 mg oxycodone or a salt thereof, said formulations providing a mean maximum plasma concentration of oxycodone from about 6 to about 60 ng/ml from a mean of about 2 to about 4.5 hours after administration, and a mean minimum plasma concentration from about 3 to about 30 ng/ml from about 10 to about 14 hours after repeated q12h administration through steady-state conditions.

The present invention is further related to controlled release oxycodone formulations comprising up to about 160 mg oxycodone or a salt thereof, said formulations providing a mean maximum plasma concentration of oxycodone up to about 240 ng/ml from a mean of about 2 to about 4.5 hours after administration, and a mean minimum plasma concentration up to about 120 ng/ml from about 10 to about 14 hours after repeated q12h administration through steady-state conditions.

BRIEF DESCRIPTION OF THE DRAWINGS

The following drawings are illustrative of embodiments of the invention and are not meant to limit the scope of the invention as encompassed by the claims.

DETAILED DESCRIPTION

It has now been surprisingly discovered that the presently claimed controlled release oxycodone formulations acceptably control pain over a substantially narrower, approximately four-fold (10 to 40 mg every 12 hours—around-the-clock dosing) in approximately 90% of patients. This is in sharp contrast to the approximately eight-fold range required for approximately 90% of patients for opioid analgesics in general.

The use of from about 10 mg to about 40 mg of 12-hourly doses of controlled-release oxycodone to control pain in approximately 90% of patients relative to a wider dosage range of other mµ-agonist analgesics, indicated for moderate to severe pain, is an example of the unique characteristics of the present invention. It should also be appreciated that the remaining 10% of patients would also be successfully managed with 12-hourly controlled-release oxycodone over a relatively narrower dosage range than with the use of other similar analgesics. Substantially all of those remaining 10% of patients not managed with controlled release oxycodone, 10 mg to 40 mg every 12 hours, would be managed using dosages of greater than 40 mg every 12 hours through 160 mg every 12 hours utilizing any one of a number or multiples of formulation strengths such as 10, 20, 40, 80 and 160 mg unit dosages or combinations thereof. In contrast, the use of other similar analgesics such as morphine would require a wider range of dosages to manage the remaining 10% of patients. For example, daily dosages of oral morphine equivalents in the range of 1 gram to more than 20 grams have been observed. Similarly, wide dosage ranges of oral hydromorphone would also be required.

Morphine, which is considered to be the prototypic opioid analgesic, has been formulated into a 12 hour controlled-release formulations (i.e., MS Contin® tablets, commercially available from Purdue Pharma, L.P.). Despite the fact that both controlled-release oxycodone and controlled release morphine administered every 12 hours around-the-clock possess qualitatively comparable clinical pharmacokinetic characteristics, the oxycodone formulations of the presently claimed invention can be used over approximately ½ the dosage range as compared to commercially available controlled release morphine formulations (such as MS Contin®) to control 90% of patients with significant pain.

Repeated dose studies with the controlled release oxycodone formulations administered every 12 hours in comparison with immediate release oral oxycodone administered every 6 hours at the same total daily dose result in comparable extent of absorption, as well as comparable maximum and minimum concentrations. The time of maximum concentration occurs at approximately 2–4.5 hours after oral administration with the controlled-release product as compared to approximately 1 hour with the immediate release product. Similar repeated dose studies with MS Contin® tablets as compared to immediate release morphine provide for comparable relative results as with the controlled release oxycodone formulations of the present invention.

There exists no substantial deviation from parallelism of the dose-response curves for oxycodone either in the forms of the controlled release oxycodone formulations of the present invention, immediate release oral oxycodone or parenteral oxycodone in comparison with oral and parenteral opioids with which oxycodone has been compared in terms of dose-response studies and relative analgesic potency assays. Beaver, et al., "Analgesic Studies of Codeine and Oxycodone in Patients with Cancer. II. Comparisons of Intramuscular Oxycodone with Intramuscular Morphine and Codeine", J. Pharmacol. and Exp. Ther., Vol. 207, No. 1, pp. 101–108, reported comparable dose-response slopes for parenteral oxycodone as compared to parenteral morphine and comparable dose-response slopes for oral as compared to parenteral oxycodone.

A review of dose-response studies and relative analgesic assays of mu-agonist opioid analgesics, which include oxycodone, morphine, hydromorphone, levorphanol, methadone, meperidine, heroin, all indicate no significant deviation from parallelism in their dose response relationships. This is so well established that it has become an underlining principal providing for establishing relative analgesic potency factors and dose ratios which are commonly utilized when converting patients from one mµ-agonist analgesic to another regardless of the dosage of the former. Unless the dose-response curves are parallel, conversion factors would not be valid across the wide range of dosages involved when substituting one drug for another.

The clinical significance provided by the controlled release oxycodone formulations of the present invention at a dosage range from about 10 to about 40 mg every 12 hours for acceptable pain management in approximately 90% of patients with moderate to severe pain, as compared to other opioid analgesics requiring approximately twice the dosage range provides for the most efficient and humane method of managing pain requiring repeated dosing. The expertise and time of physicians and nurses, as well as the duration of unacceptable pain patients must endure during the opioid analgesic titration process is substantially reduced through the efficiency of the controlled release oxycodone formulations of the present invention.

It is further clinically significant that a dose of about 80 mg controlled release oxycodone administered every 12 hours will provide acceptable pain relief management in, e.g., approximately 95% of patients with moderate to severe pain, and that about 160 mg controlled release oxycodone administered every 12 hours will provide acceptable pain relief management in, e.g., approximately all patients with moderate to severe pain.

In order to obtain a controlled release drug dosage form having at least a 12 hour therapeutic effect, it is usual in the pharmaceutical art to produce a formulation that gives a peak plasma level of the drug between about 4–8 hours after administration (in a single dose study). The present inventors have surprisingly found that, in the case of oxycodone, a peak plasma level at between 2–4.5 hours after administration gives at least 12 hours pain relief and, most surprisingly, that the pain relief obtained with such a formulation is greater than that achieved with formulations giving peak plasma levels (of oxycodone) in the normal period of up to 2 hours after administration.

A further advantage of the present composition, which releases oxycodone at a rate that is substantially independent of pH, is that it avoids dose dumping upon oral administration. In other words, the oxycodone is released evenly throughout the gastrointestinal tract.

The present oral dosage form may be presented as, for example, granules, spheroids or pellets in a capsule or in any other suitable solid form. Preferably, however, the oral dosage form is a tablet.

The present oral dosage form preferably contains between 1 and 500 mg, most especially between 10 and 160 mg, of oxycodone hydrochloride. Alternatively, the dosage form may contain molar equivalent amounts of other oxycodone salts or of the oxycodone base.

The present matrix may be any matrix that affords in vitro dissolution rates of oxycodone within the narrow ranges required and that releases the oxycodone in a pH independent manner. Preferably the matrix is a controlled release matrix, although normal release matrices having a coating that controls the release of the drug may be used. Suitable materials for inclusion in a controlled release matrix are (a) Hydrophilic polymers, such as gums, cellulose ethers, acrylic resins and protein derived materials. Of these polymers, the cellulose ethers, especially hydroxyalkylcelluloses and carboxyalkylcelluloses, are preferred. The oral dosage form may contain between 1% and 80% (by weight) of at least one hydrophilic or hydrophobic polymer.

(b) Digestible, long chain ($C_8$–$C_{50}$, especially $C_{12}$–$C_{40}$), substituted or unsubstituted hydrocarbons, such as fatty acids, fatty alcohols, glyceryl esters of fatty acids, mineral and vegetable oils and waxes. Hydrocarbons having a melting point of between 25° and 90° C. are preferred. Of these long chain hydrocarbon materials, fatty (aliphatic) alcohols are preferred. The oral dosage form may contain up to 60% (by weight) of at least one digestible, long chain hydrocarbon.

(c) Polyalkylene glycols. The oral dosage form may contain up to 60% (by weight) of at least one polyalkylene glycol.

One particular suitable matrix comprises at least one water soluble hydroxyalkyl cellulose, at least one $C_{12}$–$C_{36}$, preferably $C_{14}$–$C_{22}$, aliphatic alcohol and, optionally, at least one polyalkylene glycol.

The at least one hydroxyalkyl cellulose is preferably a hydroxy ($C_1$ to $C_6$) alkyl cellulose, such as hydroxypropylcellulose, hydroxypropylmethylcellulose and, especially, hydroxyethyl cellulose. The amount of the at least one hydroxyalkyl cellulose in the present oral dosage form will be determined, inter alia, by the precise rate of oxycodone release required. Preferably however, the oral dosage form contains between 5% and 25%, especially between 6.25% and 15% (by wt) of the at least one hydroxyalkyl cellulose.

The at least one aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the at least one aliphatic alcohol in the present oral dosage form will be determined, as above, by the precise rate of oxycodone release required. It will also depend on whether at least one polyalkylene glycol is present in or absent from the oral dosage form. In the absence of at least one polyalkylene glycol, the oral dosage form preferably contains between 20% and 50% (by wt) of the at least one aliphatic alcohol. When at least one polyalkylene glycol is present in the oral dosage form, then the combined weight of the at least one aliphatic alcohol and the at least one polyalkylene glycol preferably constitutes between 20% and 50% (by wt) of the total dosage.

In one preferred embodiment, the controlled release composition comprises from about 5 to about 25% acrylic resin and from about 8 to about 40% by weight aliphatic alcohol by weight of the total dosage form. A particularly preferred acrylic resin comprises Eudragit® RS PM, commercially available from Rohm Pharma.

In the present preferred dosage form, the ratio of, e.g., the at least one hydroxyalkyl cellulose or acrylic resin to the at least one aliphatic alcohol/polyalkylene glycol determines, to a considerable extent, the release rate of the oxycodone from the formulation. A ratio of the at least one hydroxyalkyl cellulose to the at least one aliphatic alcohol/polyalkylene glycol of between 1:2 and 1:4 is preferred, with a ratio of between 1:3 and 1:4 being particularly preferred.

The at least one polyalkylene glycol may be, for example, polypropylene glycol or, which is preferred, polyethylene glycol. The number average molecular weight of the at least one polyalkylene glycol is preferred between 1000 and 15000 especially between 1500 and 12000.

Another suitable controlled release matrix would comprise an alkylcellulose (especially ethyl cellulose), a $C_{12}$ to $C_{36}$ aliphatic alcohol and, optionally, a polyalkylene glycol.

In addition to the above ingredients, a controlled release matrix may also contain suitable quantities of other materials, e.g. diluents, lubricants, binders, granulating aids, colorants, flavorants and glidants that are conventional in the pharmaceutical art.

As an alternative to a controlled release matrix, the present matrix may be a normal release matrix having a coat that controls the release of the drug. In particularly preferred embodiments of this aspect of the invention, the present dosage form comprises film coated spheroids containing active ingredient and a non-water soluble spheronising agent. The term spheroid is known in the pharmaceutical art and means a spherical granule having a diameter of between 0.5 mm and 2.5 mm especially between 0.5 mm and 2 mm.

The spheronising agent may be any pharmaceutically acceptable material that, together with the active ingredient, can be spheronised to form spheroids. Microcrystalline cellulose is preferred.

A suitable microcrystalline cellulose is, for example, the material sold as Avicel PH 101 (Trade Mark, FMC Corporation). According to a preferred aspect of the present invention, the film coated spheroids contain between 70% and 99% (by wt), especially between 80% and 95% (by wt), of the spheronising agent, especially microcrystalline cellulose.

In addition to the active ingredient and spheronising agent, the spheroids may also contain a binder. Suitable binders, such as low viscosity, water soluble polymers, will be well known to those skilled in the pharmaceutical art. However, water soluble hydroxy lower alkyl cellulose, such as hydroxy propyl cellulose, are preferred. Additionally (or alternatively) the spheroids may contain a water insoluble polymer, especially an acrylic polymer, an acrylic copolymer, such as a methacrylic acid-ethyl acrylate copolymer, or ethyl cellulose.

The spheroids are preferably film coated with a material that permits release of the oxycodone (or salt) at a controlled rate in an aqueous medium. The film coat is chosen so as to achieve, in combination with the other ingredients, the in-vitro release rate outlined above (between 12.5% and 42.5% (by wt) release after 1 hour, etc.).

The film coat will generally include a water insoluble material such as (a) a wax, either alone or in admixture with a fatty alcohol, (b) shellac or zein, (c) a water insoluble cellulose, especially ethyl cellulose, (d) a polymethacrylate, especially Eudragit®.

Preferably, the film coat comprises a mixture of the water insoluble material and a water soluble material. The ratio of water insoluble to water soluble material is determined by, amongst other factors, the release rate required and the solubility characteristics of the materials selected.

The water soluble material may be, for example, polyvinylpyrrolidone or, which is preferred, a water soluble cellulose, especially hydroxypropylmethyl cellulose.

Suitable combinations of water insoluble and water soluble materials for the film coat include shellac and polyvinylpyrrolidone or, which is preferred, ethyl cellulose and hydroxypropylmethyl cellulose.

In order to facilitate the preparation of a solid, controlled release, oral dosage form according to this invention there is provided, in a further aspect of the present invention, a process for the preparation of a solid, controlled release, oral dosage form according to the present invention comprising incorporating hydromorphone or a salt thereof in a controlled release matrix. Incorporation in the matrix may be effected, for example, by (a) forming granules comprising at least one water soluble hydroxyalkyl cellulose and oxycodone or a oxycodone salt, (b) mixing the hydroxyalkyl cellulose containing granules with at least one $C_{12}$–$C_{36}$ aliphatic alcohol, and (c) optionally, compressing and shaping the granules. Preferably, the granules are formed by wet granulating the hydroxyalkyl cellulose/oxycodone with water. In a particularly preferred embodiment of this process, the amount of water added during the wet granulation step is preferably between 1.5 and 5 times, especially between 1.75 and 3.5 times, the dry weight of the oxycodone.

The present solid, controlled release, oral dosage form may also be prepared, in the form of film coated spheroids, by (a) blending a mixture comprising oxycodone or a oxycodone salt and a non-water soluble spheronising agent, (b) extruding the blended mixture to give an extrudate, (c) spheronising the extrudate until spheroids are formed, and (d) coating the spheroids with a film coat.

The present solid, controlled release, oral dosage form and processes for its preparation will now be described by way of example only.

DETAILED DESCRIPTION OF THE PREFERRED EMBODIMENTS

The following examples illustrate various aspects of the present invention. They are not meant to be construed to limit the claims in any manner whatsoever.

EXAMPLE 1

Controlled Release Oxycodone HCl 30 mg Tablets—Aqueous Manufacture

The required quantities of oxycodone hydrochloride, spray-dried lactose, and Eudragit® RS PM are transferred into an appropriate-size mixer, and mixed for approximately 5 minutes. While the powders are mixing, the mixture is granulated with enough water to produce a moist granular mass. The granules are then dried in a fluid bed dryer at 60° C., and then passed through an 8-mesh screen. Thereafter, the granules are redried and pushed through a 12-mesh screen. The required quantity of stearyl alcohol is melted at approximately 60°–70° C., and while the granules are mixing, the melted stearyl alcohol is added. The warm granules are returned to the mixer.

The coated granules are removed from the mixer and allowed to cool. The granules are then passed through a 12-mesh screen. The granulate is then lubricated by mixing the required quantity of talc and magnesium stearate in a suitable blender. Tablets are compressed to 375 mg in weight on a suitable tableting machine. The formula for the tablets of Example 1 is set forth in Table 1 below:

TABLE 1

| Formula of Oxycodone HCl 30-mg Tablets | | |
|---|---|---|
| Component | mg/Tablet | % (by wt) |
| Oxycodone Hydrochloride | 30.0 | 8 |
| Lactose (spray-dried) | 213.75 | 57 |
| Eudragit ® RS PM | 45.0 | 12 |
| Purified Water | q.s* | — |
| Stearyl Alcohol | 75.0 | 20 |
| Talc | 7.5 | 2 |
| Magnesium Stearate | 3.75 | 1 |
| Total: | 375.0 | 100 |

*Used in manufacture and remains in final product as residual quantity only.

The tablets of Example 1 are then tested for dissolution via the USP Basket Method, 37° C., 100 RPM, first hour 700 ml gastric fluid at pH 1.2, then changed to 900 ml at 7.5. The results are set forth in Table 2 below:

TABLE 2

| Dissolution of Oxycodone 30 mg Controlled Release Tablets | |
|---|---|
| Time | % Oxycodone Dissolved |
| 1 | 33.1 |
| 2 | 43.5 |
| 4 | 58.2 |

TABLE 2-continued

Dissolution of Oxycodone 30 mg Controlled Release Tablets

| Time | % Oxycodone Dissolved |
|---|---|
| 8 | 73.2 |
| 12 | 81.8 |
| 18 | 85.8 |
| 24 | 89.2 |

EXAMPLE 2

Controlled Oxycodone HCl 10 mg Release Tablets—Organic Manufacture

The required quantities of oxycodone hydrochloride and spray dried lactose are transferred into an appropriate sized mixer and mix for approximately 6 minutes. Approximately 40 percent of the required Eudragit® RS PM powder is dispersed in Ethanol. While the powders are mixing, the powders are granulated with the dispersion and the mixing continued until a moist granular mass is formed. Additional ethanol is added if needed to reach granulation end point. The granulation is transferred to a fluid bed dryer and dried at 30° C.; and then passed through a 12-mesh screen. The remaining Eudragit® RS PM is dispersed in a solvent of 90 parts ethanol and 10 parts purified water; and sprayed onto the granules in the fluid bed granulator/dryer at 30° C. Next, the granulate is passed through a 12-mesh screen. The required quantity of stearyl alcohol is melted at approximately 60°–70° C. The warm granules are returned to the mixer. While mixing, the melted stearyl alcohol is added. The coated granules are removed from the mixer and allowed to cool. Thereafter, they are passed through a 12-mesh screen.

Next, the granulate is lubricated by mixing the required quantities of talc and magnesium stearate in a suitable blender. The granulate is then compressed to 125 mg tablets on a suitable tableting machine.

The formula for the tablets of Example 2 (10 mg controlled release oxycodone) is set forth in Table 3 below:

TABLE 3

Formula of Oxycodone HCl 10 mg Controlled Release Tablets

| Component | Mg/Tablet | Percent (by wt) |
|---|---|---|
| Oxycodone hydrochloride | 10.00 | 8 |
| Lactose (spray-dried) | 71.25 | 57 |
| Eudragit® RS PM | 15.00 | 12 |
| Ethanol | q.s.* | — |
| Purified Water | q.s.* | — |
| Stearyl Alcohol | 25.00 | 20 |
| Talc | 2.50 | 2 |
| Magnesium stearate | 1.25 | 1 |
| Total: | 125.00 mg | 100 |

*Used only in the manufacture and remains in final product as residual quantity only.

The tablets of Example 2 are then tested for dissolution via USP Basket Method at 37° C., 100 RPM, first hour 700 ml simulated gastric (pH 1.2) then changed to 900 ml at pH 7.5.

The results are set forth in Table 4 below:

TABLE 4

Dissolution of Oxycodone 10 mg Controlled Release Tablets

| Hour | % Dissolved |
|---|---|
| 1 | 35.9 |
| 2 | 47.7 |
| 4 | 58.5 |
| 8 | 67.7 |
| 12 | 74.5 |
| 18 | 76.9 |
| 24 | 81.2 |

EXAMPLES 3–4

Controlled Release Oxycodone 10 and 20 mg Tablets (Aqueous Manufacture)

Eudragit® RS 30D and Triacetin® are combined while passing though a 60 mesh screen, and mixed under low shear for approximately 5 minutes or until a uniform dispersion is observed.

Next, suitable quantities of Oxycodone HCl, lactose, and povidone are placed into a fluid bed granulator/dryer (FBD) bowl, and the suspension sprayed onto the powder in the fluid bed. After spraying, the granulation is passed through a #12 screen if necessary to reduce lumps. The dry granulation is placed in a mixer.

In the meantime, the required amount of stearyl alcohol is melted at a temperature of approximately 70° C. The melted stearyl alcohol is incorporated into the granulation while mixing. The waxed granulation is transferred to a fluid bed granulator/dryer or trays and allowed to cool to room temperature or below. The cooled granulation is then passed through a #12 screen. Thereafter, the waxed granulation is placed in a mixer/blender and lubricated with the required amounts of talc and magnesium stearate for approximately 3 minutes, and then the granulate is compressed into 125 mg tablets on a suitable tableting machine.

The formula for the tablets of Example 3 is set forth in Table 5 below:

TABLE 5

Formula of Controlled Release Oxycodone 10 mg Tablets

| Component | Mg/Tablet | % (by wt) |
|---|---|---|
| Oxycodone Hydrochloride | 10.0 | 8.0 |
| Lactose (spray dried) | 69.25 | 55.4 |
| Povidone | 5.0 | 4.0 |
| Eudragit® RS 30D (solids) | 10.0* | 8.0 |
| Triacetin® | 2.0 | 1.6 |
| Stearyl Alcohol | 25.0 | 20.0 |
| Talc | 2.5 | 2.0 |
| Magnesium Stearate | 1.25 | 1.0 |
| Total: | 125.0 | 100.0 |

*Approximately 33.33 mg Eudragit® RS 30D Aqueous dispersion is equivalent to 10 mg of Eudragit® RS 30D dry substance.

The tablets of Example 3 are then tested for dissolution via the USP Basket Method at 37° C., 100 RPM, first hour 700 ml simulated gastric fluid at pH 1.2, then changed to 900 ml at pH 7.5. The results are set forth in Table 6 below:

TABLE 6

Dissolution of Oxycodone 10 mg
Controlled Release Tablets

| Hour | % Oxycodone Dissolved |
|---|---|
| 1 | 38.0 |
| 2 | 47.5 |
| 4 | 62.0 |
| 8 | 79.8 |
| 12 | 91.1 |
| 18 | 94.9 |
| 24 | 98.7 |

The formula for the tablets of Example 4 is set forth in Table 7 below:

TABLE 7

Formula of Controlled Release Oxycodone 20 mg Tablets

| Component | Mg/Tablet |
|---|---|
| Oxycodone Hydrochloride | 20.0 |
| Lactose (spray dried) | 59.25 |
| Povidone | 5.0 |
| Eudragit ® RS 30D (solids) | 10.0* |
| Triacetin ® | 2.0 |
| Stearyl Alcohol | 25.0 |
| Talc | 2.5 |
| Magnesium Stearate | 1.25 |
| Total: | 125.0 |

The tablets of Example 4 are then tested for dissolution via the USP Basket Method at 37° C., 100 RPM, first hour 700 ml simulated gastric fluid at pH 1.2, then changed to 900 ml at pH 7.5. The results are set forth in Table 8 below:

TABLE 8

Dissolution of Oxycodone 20 mg Controlled Release Tablets

| Hour | % Oxycodone Dissolved |
|---|---|
| 1 | 31 |
| 2 | 44 |
| 4 | 57 |
| 8 | 71 |
| 12 | 79 |
| 18 | 86 |
| 24 | 89 |

EXAMPLES 5–6

In Example 5, 30 mg controlled release oxycodone hydrochloride tablets are prepared according to the process set forth in Example 1.

In Example 6, 10 mg controlled release oxycodone hydrochloride tablets are prepared according to the process set forth in Example 2.

Thereafter, dissolution studies of the tablets of Examples 5 and 6 are conducted at different pH levels, namely, pH 1.3, 4.56, 6.88 and 7.5.

The results are provided in Tables 9 and 10 below:

TABLE 9

Example 5
Percentage Oxycodone HCl
30 mg Tablets Dissolved Over Time

| pH | 1 | 2 | 4 | 8 | 12 | 18 | 24 |
|---|---|---|---|---|---|---|---|
| 1.3 | 29.5 | 43.7 | 61.8 | 78.9 | 91.0 | 97.0 | 97.1 |
| 4.56 | 34.4 | 49.1 | 66.4 | 82.0 | 95.6 | 99.4 | 101.1 |
| 6.88 | 33.8 | 47.1 | 64.4 | 81.9 | 92.8 | 100.5 | 105.0 |
| 7.5 | 27.0 | 38.6 | 53.5 | 70.0 | 81.8 | 89.7 | 96.6 |

TABLE 10

Example 6
Percentage Oxycodone HCl - 10 mg
Tablets Dissolved Over Time

| pH | 1 | 2 | 4 | 8 | 12 | 18 | 24 |
|---|---|---|---|---|---|---|---|
| 1.3 | 25.9 | 41.5 | 58.5 | 73.5 | 85.3 | 90.7 | 94.2 |
| 4.56 | 37.8 | 44.2 | 59.4 | 78.6 | 88.2 | 91.2 | 93.7 |
| 6.88 | 34.7 | 45.2 | 60.0 | 75.5 | 81.4 | 90.3 | 93.9 |
| 7.5 | 33.2 | 40.1 | 51.5 | 66.3 | 75.2 | 81.7 | 86.8 |

EXAMPLES 7–12

In Examples 7–12, 4 mg and 10 mg oxycodone HCl tablets were prepared according to the formulations and methods set forth in the assignee's U.S. Pat. No. 4,990,341.

In Example 7, oxycodone hydrochloride (10.00 gm) was wet granulated with lactose monohydrate (417.5 gm) and hydroxyethyl cellulose (100.00 gm), and the granules were sieved through a 12 mesh screen. The granules were then dried in a fluid bed dryer at 50° C. and sieved through a 16 mesh screen.

Molten cetostearyl alcohol (300.0 gm) was added to the warmed oxycodone containing granules, and the whole was mixed thoroughly. The mixture was allowed to cool in the air, regranulated and sieved through a 16 mesh screen.

Purified Talc (15.0 gm) and magnesium stearate (7.5 gm) were then added and mixed with the granules. The granules were then compressed into tablets.

Example 8 is prepared in the same manner as Example 7; however, the formulation includes 10 mg oxycodone HCl/tablet. The formulas for Examples 7 and 8 are set forth in Tables 11 and 12, respectively.

TABLE 11

Formulation of Example 7

| Ingredient | mg/tablet | g/batch |
|---|---|---|
| Oxycodone hydrochloride | 4.0 | 10.0 |
| Lactose monohydrate | 167.0 | 417.5 |
| Hydroxyethylcellulose | 40.0 | 100.0 |
| Cetostearyl alcohol | 120.0 | 300.0 |
| Purified talc | 6.0 | 15.0 |
| Magnesium stearate | 3.0 | 7.5 |

TABLE 12

| Formulation of Example 8 | | |
| --- | --- | --- |
| Ingredient | mg/tablet | g/batch |
| Oxycodone hydrochloride | 10.0 | 25.0 |
| Lactose monohydrate | 167.0 | 417.5 |
| Hydroxyethylcellulose | 40.0 | 100.0 |
| Cetostearyl alcohol | 120.0 | 300.0 |
| Talc | 6.0 | 15.0 |
| Magnesium stearate | 3.0 | 7.5 |

In Example 9, 4 mg oxycodone HCl controlled release tablets are prepared according to the excipient formula cited in Example 2 of U.S. Pat. No. 4,990,341. The method of manufacture is the same as set forth in Examples 7 and 8 above. Example 10 is prepared according to Example 9, except that 10 mg oxycodone HCl is included per tablet. The formulas for Examples 9 and 10 are set forth in Tables 13 and 14, respectively.

TABLE 13

| Formulation of Example 9 | | |
| --- | --- | --- |
| Ingredient | mg/tablet | g/batch |
| Oxycodone hydrochloride | 4.0 | 10.0 |
| Anhydrous Lactose | 167.0 | 417.5 |
| Hydroxyethylcellulose | 30.0 | 75.0 |
| Cetostearyl alcohol | 90.0 | 225.0 |
| Talc | 6.0 | 15.0 |
| Magnesium stearate | 3.0 | 7.5 |

TABLE 14

| Formulation of Example 14 | | |
| --- | --- | --- |
| Ingredient | mg/tablet | g/batch |
| Oxycodone hydrochloride | 10.0 | 25.0 |
| Hydrous lactose | 167.0 | 417.5 |
| Hydroxyethylcellulose | 30.0 | 75.0 |
| Cetostearyl alcohol | 90.0 | 225.0 |
| Talc | 6.0 | 15.0 |
| Magnesium stearate | 3.0 | 7.5 |

In Example 11, oxycodone 4 mg controlled release tablets are prepared with the same excipient formula cited in Example 3 of U.S. Pat. No. 4,990,341.

Oxycodone hydrochloride (32.0 gm) was wet granulated with lactose monohydrate (240.0 gm) hydroxyethyl cellulose (80.0 gm) and methacrylic acid copolymer (240.0 gm, Eudragit® L-100-55), and the granules were sieved through a 12 mesh screen. The granules were then dried in a Fluid Bed Dryer at 50° C. and passed through a 16 mesh screen.

The warmed oxycodone containing granules was added molten cetostearyl alcohol (240.0 gm), and the whole was mixed thoroughly. The mixture was allowed to cool in the air, regranulated and sieved through a 16 mesh screen. The granules were then compressed into tablets.

Example 12 is prepared in identical fashion to Example 11, except that 10 mg oxycodone HCl is included per tablet. The formulations for Examples 11 and 12 are set forth in Tables 15 and 16, respectively.

TABLE 15

| Formulation of Example 11 | | |
| --- | --- | --- |
| Ingredient | mg/tablet | g/batch |
| Oxycodone hydrochloride | 4.0 | 32.0 |
| Lactose monohydrate | 30.0 | 240.5 |
| Hydroxyethylcellulose | 10.0 | 80.0 |
| Methacrylic acid copolymer | 30.0 | 240.0 |
| Cetostearyl alcohol | 30.0 | 240.0 |

TABLE 16

| Formulation of Example 12 | | |
| --- | --- | --- |
| Ingredient | mg/tablet | g/batch |
| Oxycodone hydrochloride | 10.0 | 80.0 |
| Lactose monohydrate | 30.0 | 240.5 |
| Hydroxyethylcellulose | 10.0 | 80.0 |
| Methacrylic acid copolymer | 30.0 | 240.0 |
| Cetostearyl alcohol | 30.0 | 240.0 |

Next, dissolution studies were conducted on the tablets of Examples 7–12 using the USP basket method as described in the U.S. Pharmacopoeia XXII (1990). The speed was 100 rpm, the medium was simulated gastric fluid for the first hour followed by simulated intestinal fluid thereafter, at a temperature of 37° C. Results are given in Table 17.

TABLE 17

| DISSOLUTION STUDIES OF EXAMPLES 7–12 | | | | | | |
| --- | --- | --- | --- | --- | --- | --- |
| Time | % Oxycodone Dissolved | | | | | |
| (hrs) | Ex. 7 | Ex. 8 | Ex. 9 | Ex. 10 | Ex. 11 | Ex. 12 |
| 1 | 23.3 | 25.5 | 28.1 | 29.3 | 31.3 | 40.9 |
| 2 | 35.6 | 37.5 | 41.5 | 43.2 | 44.9 | 55.6 |
| 4 | 52.9 | 56.4 | 61.2 | 63.6 | 62.1 | 74.2 |
| 8 | 75.3 | 79.2 | 83.7 | 88.0 | 82.0 | 93.9 |
| 12 | 90.7 | 94.5 | 95.2 | 100.0 | 91.4 | 100.0 |

EXAMPLES 13–16

Clinical Studies

In Examples 13–16, randomized crossover bioavailability studies were conducted employing the formulation of Examples 2 (organic manufacture) and 3 (aqueous manufacture).

In Example 13, a single dose fast/fed study was conducted on 24 subjects with oxycodone tablets prepared according to Example 3.

In Example 14, a steady-state study was conducted on 23 subjects after 12 hours with oxycodone tablets prepared according to Example 2, and compared to a 5 mg oxycodone immediate-release solution.

In Example 15, a single dose study was conducted on subjects using oxycodone tablets prepared according to Example 3, and compared to a 20 mg oxycodone immediate release solution.

In Example 16, a 12 subject single-dose study was conducted using 3×10 mg oxycodone tablets prepared according to Example 3, and compared to a 30 mg oxycodone immediate release solution.

The results of Examples 13–16 are set forth in Table 18.

TABLE 18

| Example | Dosage | AUC ng/ml/hr | Cmax ng/ml | Tmax hr |
|---|---|---|---|---|
| 13 | 10 mg CR Fast | 63 | 6.1 | 3.8 |
|  | 10 mg CR Fed | 68 | 7.1 | 3.6 |
| 14 | 5 mg IR q6h | 121 | 17 | 1.2 |
|  | 10 mg CR q12h | 130 | 17 | 3.2 |
| 15 | 20 mg IR | 188 | 40 | 1.4 |
|  | 2 × 10 mg CR | 197 | 18 | 2.6 |
| 16 | 30 mg IR | 306 | 53 | 1.2 |
|  | 3 × 10 mg CR | 350 | 35 | 2.6 |
|  | 30 mg CR | 352 | 36 | 2.9 |

IR denotes immediate-release oxycodone solution.
CR denotes controlled-release tablets

EXAMPLE 17

Clinical Studies

In Example 17, a single dose, double blind, randomized study determined the relative analgesic efficacy, the acceptability, and relative duration of action of an oral administration of controlled release oxycodone 10, 20 and 30 mg prepared according to the present invention (CR OXY) compared to immediate release oxycodone 15 mg (IR OXY), immediate release oxycodone 10 mg in combination with acetaminophen 650 mg (IR OXY/APAP) and placebo in 180 patients with moderate or severe pain following abdominal or gynecological surgery. Patients rated their pain intensity and pain relief hourly for up to 12 hours postdosing. Treatments were compared using standard scales for pain intensity and relief, and onset and duration of pain relief.

All active treatments were significantly superior to placebo for many of the hourly measures, and for sum pain intensity differences (SPID) and total pain relief (TOTPAR). A dose response was seen among the 3 dose levels of CR OXY for pain relief and peak pain intensity difference (PID), with CR OXY 20 mg and 30 mg being significantly better than the 10 mg dose. IR OXY was significantly superior to CR OXY 10 mg at hr 1 and 2. IR OXY/APAP was significantly superior to the 3 doses of CR OXY at hr 1, and to CR OXY 10 mg at hrs 2 through 5. Onset time was significantly shorter for the IR OXY and IR OXY/APAP treatment groups in comparison to the 3 CR OXY treatments. The distribution functions for duration of relief revealed significantly longer duration of relief for the three CR OXY doses than for IR OXY and IR OXY/APAP. No serious adverse experiences were reported. The results are more particularly reported in Table 19 below.

TABLE 19

| | PATIENT DISPOSITION TREATMENT GROUP | | | | | | |
|---|---|---|---|---|---|---|---|
| | IR OXY | | CR OXY | | | | |
| | 15 mg | PLACEBO | 10 mg | 20 mg | 30 mg | 2 PERC* | TOTAL |
| Enrolled and Randomized to Study Treatment | 31 | 31 | 30 | 30 | 30 | 30 | 182 |
| Entered the Study Treatment Phase | 31 | 31 | 30 | 30 | 30 | 30 | 182 |
| Completed the Study | 31 | 30 | 30 | 30 | 30 | 30 | 181 |
| Discontinued from the Study | 0 | 1 | 0 | 0 | 0 | 0 | 1 |
| Excluded from Efficacy Analysis Vomited prior to 1 hr post dose | 0 | 1 | 0 | 0 | 0 | 0 | 1 |
| Inadvertently received rescue during study | 1 | 0 | 0 | 0 | 0 | 0 | 1 |
| Analysis Population: Evaluable for Safety and Efficacy | 30 | 30 | 30 | 30 | 30 | 30 | 180 |
| Evaluable for Safety | 31 | 31 | 30 | 30 | 30 | 30 | 182 |

*2 tablets of Percocet ®

The time-effect curves for pain intensity, pain intensity differences and pain relief are shown in FIGS. 1–4. CR OXY 10 mg had significantly ($p<0.05$) lower pain intensity scores than the placebo-treated patients at hours 3–11 and lower pain scores than IR OXY 15 mg and Percocet® at hour 10. CR OXY 20 mg has significantly ($p<0.05$) lower pain intensity scores compared to placebo at hours 2–11 and significantly (p<0.05) lower pain scores than CR OXY 10 mg, IR OXY 15 mg and Percocet at hours 9–11. CR OXY 30 mg had significantly (p<0.05) lower pain scores than placebo at hours 2–11 and lower pain scores than CR OXY 10 mg at hours 2, 3, and 5 and lower scores than Percocet® at hour 10.

For hourly pain relief scores categorical and visual analog scales (CAT and VAS), CR OXY 10 mg had significantly (p<0.05) higher pain relief scores than placebo at hours 3–11 and higher relief scores than. IR OXY and Percocet® at hour 10 (and Percocet® at hour 11). CR OXY 20 mg had significantly (p<0.05) higher relief scores than placebo at hours 2–12 and higher relief scores than Percocet® at hours 9–12. In addition, CR OXY had significantly (p<0.05) higher pain relief than IR OXY at hours 10–12. CR OXY 30 mg had significantly (p<0.05) higher pain relief scores than placebo at hours 2–12 and higher scores than Percocet® at hours 9–12 and IR OXY 15 mg at hour 10.

Each treatment group was significantly (p<0.05) better than placebo with respect to the sum of the pain intensity differences (SPID) and total pain relief (TOTPAR).

Duration of pain relief as measured by the patient stopwatch method showed that CR OXY 10 mg, 20 mg and 30 mg had significantly (p<0.05) longer duration of action compared to IR OXY 15 mg and 2 tablets Percocet®. In addition, the three controlled-release formulations had significantly (p<0.05) longer times to remedication compared to Percocet®.

Before remedication, a total of 104 (57%) of patients reported 120 adverse experiences. The most common were somnolence, fever, dizziness and headache.

Based upon the results of this study it is concluded that the controlled release oxycodone formulations of the present invention relieve moderate to severe postoperative pain, e.g., due to abdominal or gynecological surgery in women. There is a dose response noted in which placebo<10 mg<20 mg<30 mg CR OXY following a single dose. Onset of action occurred in one hour with peak effects noted from 2 to 5 hours and a duration of effect from 10 to 12 hours. In the chronic pain situation steady state dosing may prolong this effect. Side effects are expected and easily managed. Headache may be related to dose. Dizziness and somnolence were reported.

IR OXY 15 mg has an intermediate peak effect compared to controlled release oxycodone. Its duration of action is shorter (6–8 hours). Percocet® is quite effective in terms of onset, peak effect and safety. The duration of action is 6–8 hours.

In summary, CR OXY was clearly an effective oral analgesic, with a slower onset but a longer duration of effect than either IR OXY or IR OXY/APAP.

EXAMPLE 18

Clinical Studies

In Example 18, a steady state crossover trial was conducted in 21 normal male subjects comparing a. CR OXY 10 mg administered every 12 hours (q12h); and b. Roxicodone® oral solution 5 mg (ROX) administered every 6 hours (q6h), Treatment (b) was the study reference standard. The average age was 34 years, height 176 cm and weight 75 kg. No unusual features were noted about the group.

Figure 1:
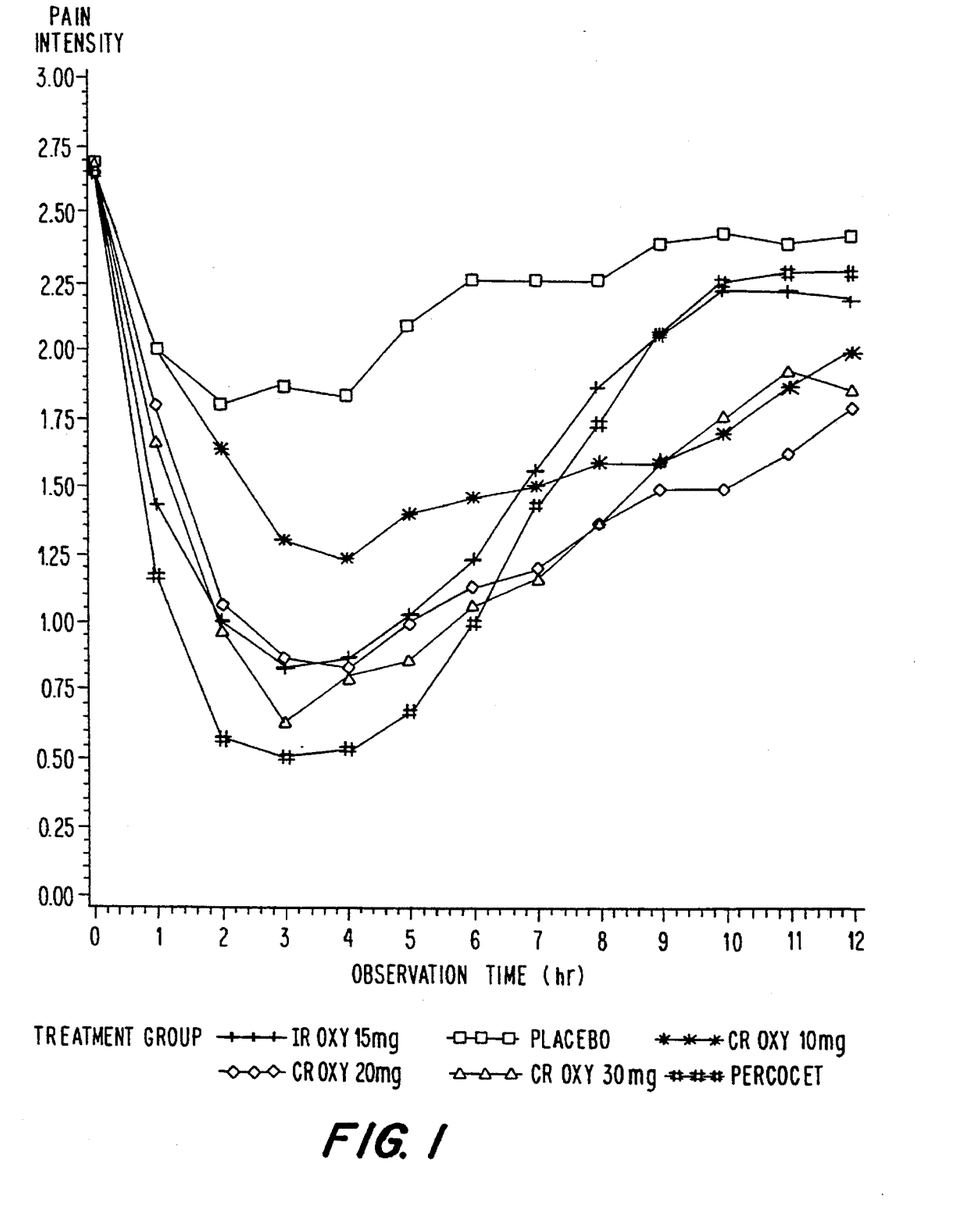
FIGS. 1–4 are graphs showing the time-effect curves for pain intensity differences and pain relief for Example 17.
Figure 2:
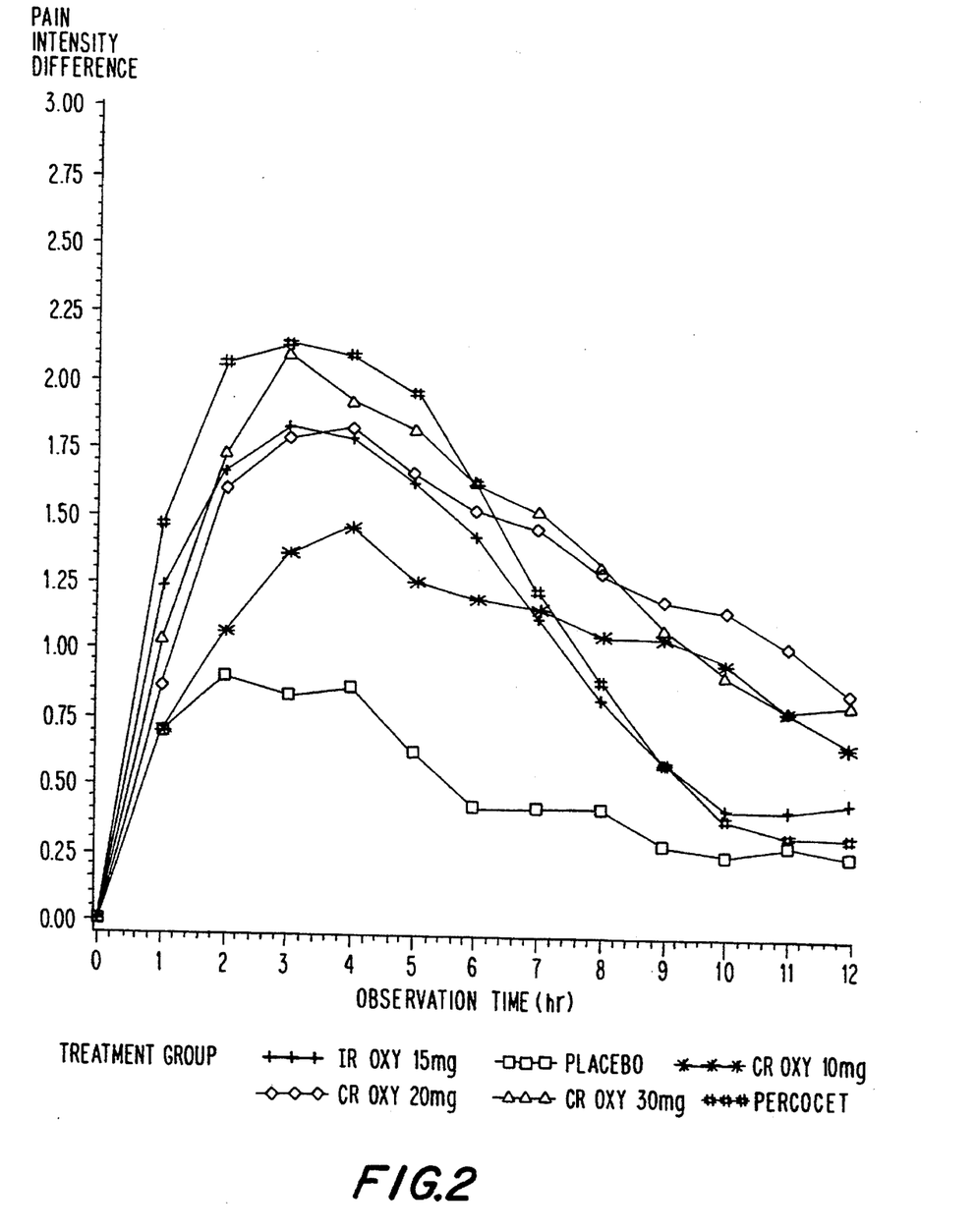
Figure 3:
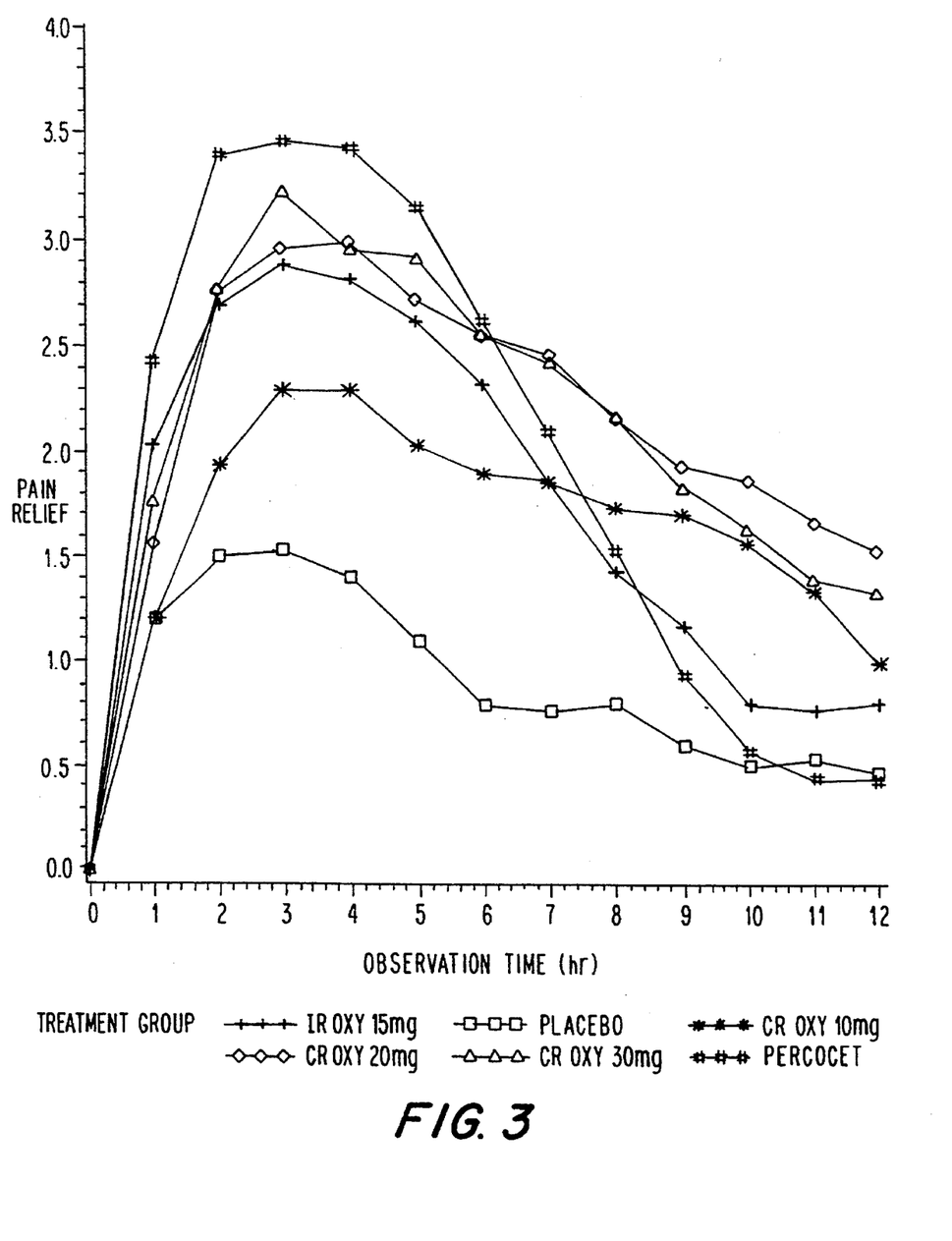
Figure 4:
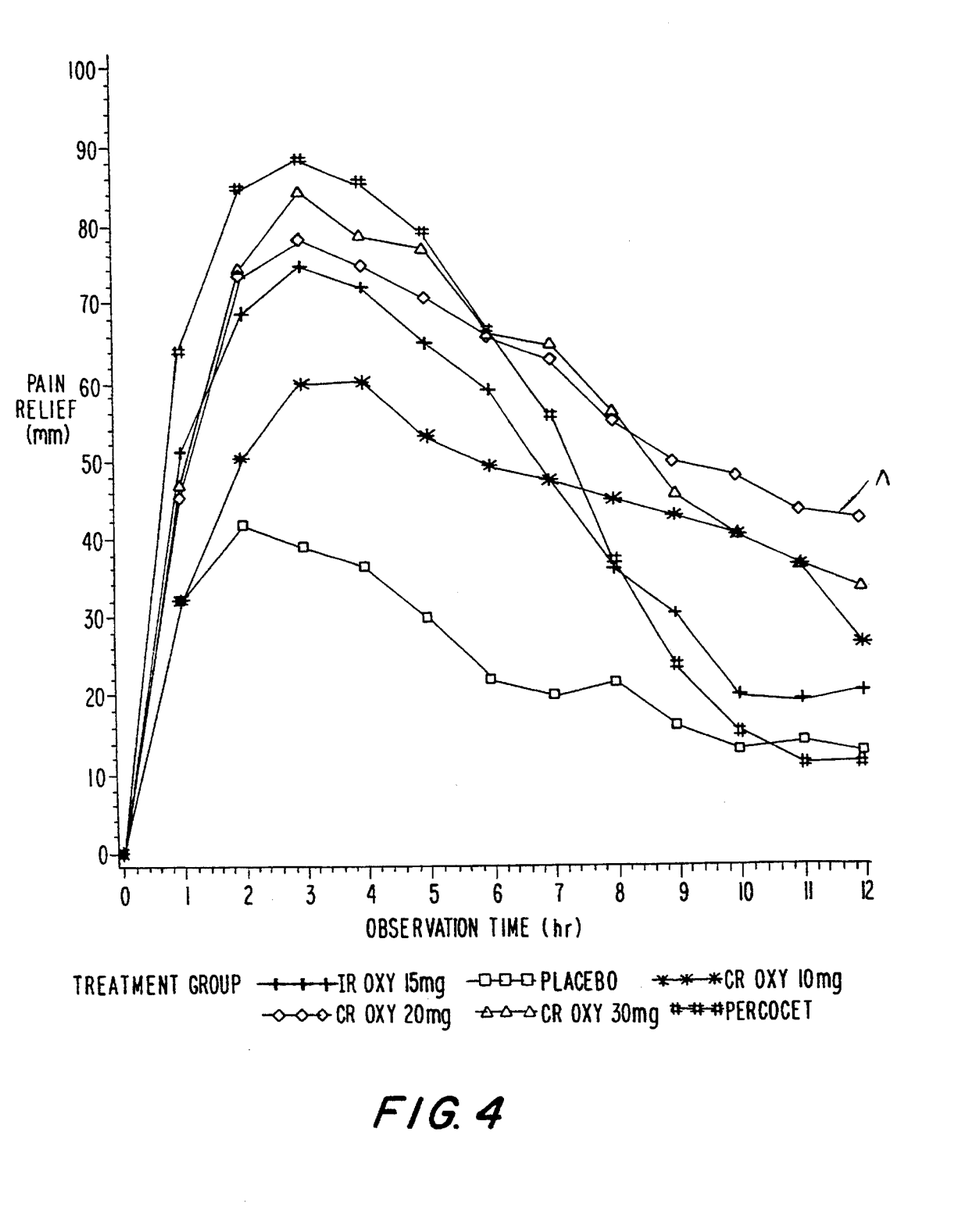
Figure 5:
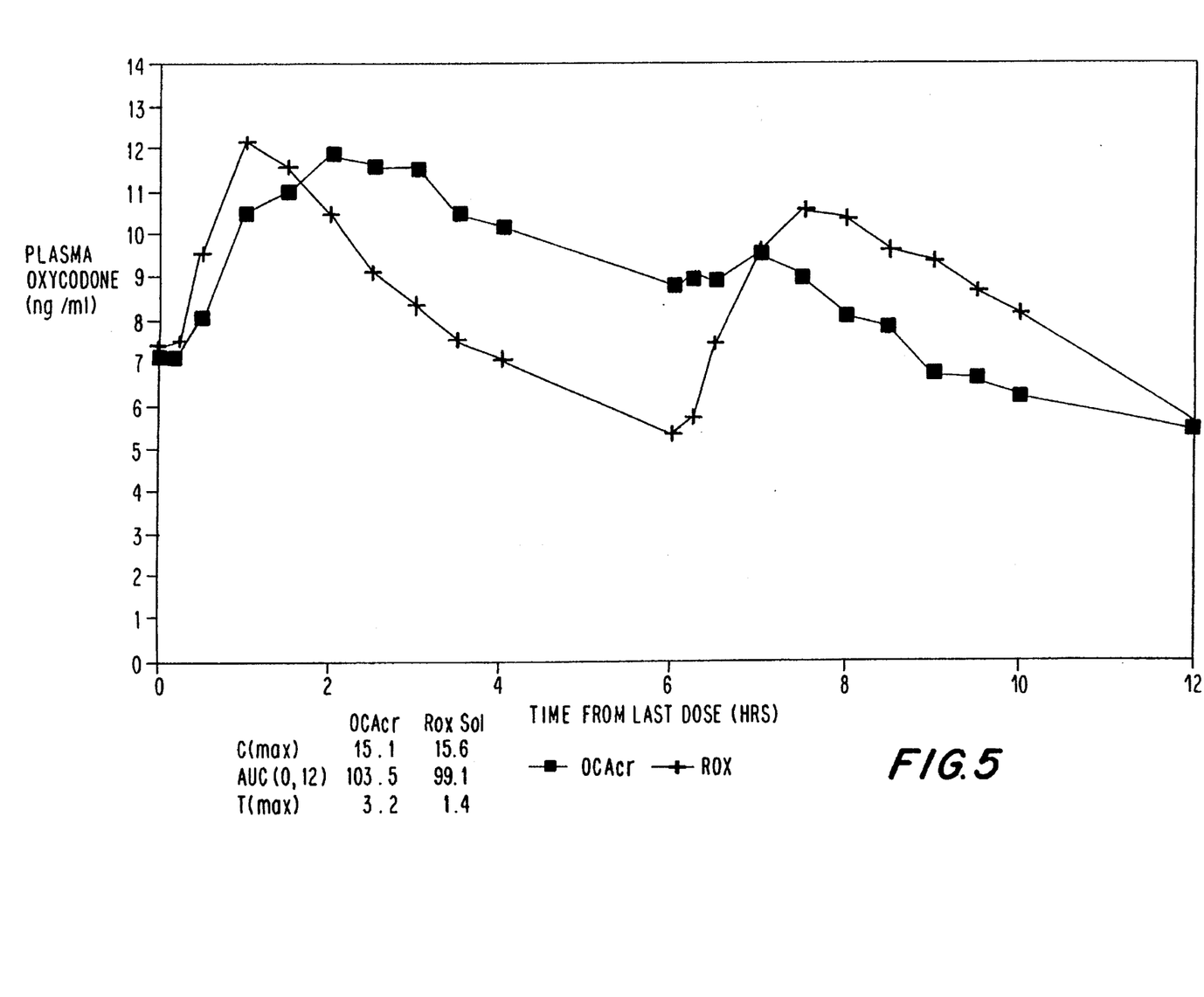
FIG. 5 is a graph showing the mean plasma oxycodone concentration for a 10 mg controlled release oxycodone formulation prepared in accordance with the present invention and a study reference standard.

FIG. 5 shows the mean plasma oxycodone concentrations for the two formulations over the 12 hour dosing interval. The results are summarized in Table 18 in terms of mean values, ratios of mean values and 90% confidence intervals.

As inspection of Table 18 reveals, with one exception, no significant differences were detected between the two formulations. The single exception is the mean $t_{max}$ for CR OXY of 3.18 hours which, as expected for a controlled release formulation, significantly exceeded the ROX mean of 1.38 hours. Mean AUC-based bioavailability, (ROX= 100%) was 104.4% with 90% confidence limits of 90.9 to 117.9%. Thus, the FDA specification of ±20% is met so that the study results support an assertion of equal oxycodone availability.

TABLE 20

SUMMARY OF PHARMACOKINETIC PARAMETERS FOR OXYCODONE FOLLOWING A SINGLE DOSE OF CR OXY (10 mg q 12H) AND ROXICODONE ® ORAL SOLUTION (5 mg q 6h)

| PARAMETER | CR OXY | ROXICODONE SOLUTION | OXY/ROXI (%) | 90% CI* |
|---|---|---|---|---|
| $C_{max}$ (ng/mL) | | | | |
| ARITH. MEAN (SD) | 15.11(4.69) | 15.57(4.41) | 97.08 | 85.59–108.50 |
| GEOMETRIC MEAN | 14.43 | 15.01 | 95.14 | |
| $C_{min}$ (ng/mL) | | | | |
| ARITH. MEAN (SD) | 6.24(2.64) | 6.47(3.07) | 96.41 | 80.15–112.74 |
| GEOMETRIC MEAN | 5.62 | 5.83 | 96.48 | |
| $t_{max}$ (hrs) ARITH. MEAN (SD) | 3.18(2.21) | 1.38(0.71)* | 230.17 | 160.71–298.71 |
| AUC (0–12 hrs) | | | | |
| ARITH. MEAN (SD) | 103.50(40.03) | 99.10(35.04) | 104.44 | 90.92–117.94 |
| GEOMETRIC MEAN | 97.06 | 93.997 | 103.29 | |
| % Swing ARITH. MEAN | 176.36(139.0) | 179.0(124.25) | 98.53 | 62.06–134.92 |

TABLE 20-continued

SUMMARY OF PHARMACOKINETIC PARAMETERS FOR OXYCODONE FOLLOWING A SINGLE DOSE OF CR OXY (10 mg q 12H) AND ROXICODONE ® ORAL SOLUTION (5 mg q 6h)

| PARAMETER | CR OXY | ROXICODONE SOLUTION | OXY/ROXI (%) | 90% CI* |
|---|---|---|---|---|
| (SD) | | | | |
| % Fluctuation ARITH. MEAN (SD) | 108.69(38.77) | 117.75(52.47) | 92.22 | 76.81–107.57 |
| End Point ARITH. MEAN (SD) | −1.86(2.78) | −1.86(2.19) | 99.97 | 117.77–22.23 |

*90% Confidence Interval
--Signicant Difference p < 0.05

EXAMPLE 19

Clinical Studies

In Example 19, twenty-four normal, healthy male subjects were enrolled in a randomized single-dose two-way crossover study to compare the plasma oxycodone concentrations obtained after dosing with two controlled-release oxycodone 10 mg tablets versus 20 mg (20 ml of 5 mg/5 ml) of immediate release (IR) oxycodone hydrochloride solution. Twenty-three subjects completed the study and were eligible for analysis.

Plasma oxycodone concentrations were determined by a high performance liquid chromatographic procedure. Arithmetic Mean $C_{max}$, $t_{max}$, AUC, and half-lives calculated from individual plasma oxycodone concentration-versus-time data are set forth in Table 21:

TABLE 21

| Pharmacokinetic Parameter | Reference Product IR Oxycodone 20 mg | Test Product CR Oxycodone 2 × 10 mg | F. (%) | 90% Confidence Interval |
|---|---|---|---|---|
| $C_{max}$ (ng/ml) | 41.60 | 18.62 | 44.75 | 32.5–57.0 |
| $t_{max}$ (hours) | 1.30 | 2.62 | 200.83 | 169.8–232.6 |
| AUC (0–36) (mg × hr/ml) | 194.35 | 199.62 | 102.71 | 89.5–115.9 |
| AUC (0–∞) (ng × hr/ml) | 194.38 | 208.93 | 107.49 | 92.9–121.9 |
| $t_{½(elim)}$ (hrs) | 3.21 | 7.98* | 249.15 | 219.0–278.8 |
| $t_{½(abs)}$ (hrs) | 0.35 | 0.92* | 264.17 | 216.0–310.7 |

F. % = Oral bioavailability (CR oxycodone 2 × 10 mg/IR oxycodone 20 mg)
*Statistically significant (p = 0.0001)

For $C_{max}$, $t_{max}$, $t_{1/2}$(elim) and $t_{1/2}$(abs) there were statistically significant differences between the CR OXY and IR OXY. There were no statistically significant differences between the two treatments in the extent of absorption [AUC (0,36), AUC (0,∞). The 90% confidence interval for CR OXY relative to IR OXY relative was 89.5%–115.9% for AUC (0,36) and 92.9%–121.9% for AUC (0,∞). Based on the 90% confidence interval analysis, the controlled-release oxycodone tablets were equivalent in extent of absorption (AUC 0,36) to the immediate-release oxycodone solution. The controlled-release oxycodone absorption was slower by approximately 1.3 hours. No statistically significant differences were noted between the two treatments with reference to adverse experiences, none of which were considered clinically unusual for opiates for this type of study.

The above studies demonstrate a significant dose-response relationship utilizing the controlled release oxycodone formulations of the present invention at dosages of 10, 20 and 30 mg which does not deviate from parallelism with dose-response slopes for MS Contin in similarly designed well-controlled analgesic efficacy studies of MS Contin reported by Kaiko R. S., Van Wagoner D., Brown J., et al., "Controlled-Release Oral Morphine (MS Contin® Tablets MSC) in Postoperative Pain", Pain Suppl., 5:S149 1990, who compared 30, 60, 90, and 120 mg of MS Contin as compared with 10 mg of intramuscular morphine and placebo and Bloomfield, et al., "Analgesic Efficacy and Potency of Two Oral Controlled-Release Morphine Preparations", Clinical Pharmacology & Therapeutics, (in press), who compared 30 and 90 mg of MS Contin as compared to 30 and 90 mg of another controlled-release oral morphine preparation, Oramorph SR 30 mg tablets.

The examples provided above are not meant to be exclusive. Many other variations of the present invention would be obvious to those skilled in the art, and are contemplated to be within the scope of the appended claims.

What is claimed is:

1. A controlled release oxycodone formulation for oral administration to human patients, comprising from about 10 to about 40 mg oxycodone or a salt thereof, said formulation providing a mean maximum plasma concentration of oxycodone from about 6 to about 60 ng/ml from a mean of about 2 to about 4.5 hours after administration, and a mean minimum plasma concentration from about 3 to about 30 ng/ml from a mean of about 10 to about 14 hours after repeated administration every 12 hours through steady-state conditions.

2. A controlled release oxycodone formulation for oral administration to human patients, comprising from about 10 mg to about 160 mg oxycodone or a salt thereof, said formulation providing a mean maximum plasma concentration of oxycodone from about 6 to about 240 ng/ml from a mean of about 2 to about 4.5 hours after administration, and a mean minimum plasma concentration from about 3 to about 120 ng/ml from a mean of about 10 to about 14 hours after repeated administration every 12 hours through steady-state conditions.

3. A solid controlled release oral dosage form, comprising
    (a) oxycodone or a salt thereof in an amount from about 10 to about 160 mg;

(b) an effective amount of a controlled release matrix selected from the group consisting of hydrophilic polymers, hydrophobic polymers, digestible substituted or unsubstituted hydrocarbons having from about 8 to about 50 carbon atoms, polyalkylene glycols, and mixtures of any of the foregoing; and (c) a suitable amount of a suitable pharmaceutical diluent, wherein said composition provides a mean maximum plasma concentration of oxycodone from about 6 to about 240 ng/ml from a mean of about 2 to about 4.5 hours after administration, and a mean minimum plasma concentration from about 3 to about 120 ng/ml from a mean of about 10 to about 14 hours after repeated administration every 12 hours through steady-state conditions.

4. The controlled release composition of claim 3, wherein said controlled release matrix comprises an acrylic resin.

5. A solid controlled release oral dosage form, comprising (a) an analgesically effective amount of spheroids comprising oxycodone or a salt thereof and either a spheronising agent or an acrylic polymer or copolymer, such that the total dosage of oxycodone in said dosage form is from about 10 to about 160 mg;

(b) a film coating which controls the release of the oxycodone or oxycodone salt at a controlled rate in an aqueous medium, wherein said composition provides an in vitro dissolution rate of the dosage form;

said composition providing a mean maximum plasma concentration of oxycodone from about 6 to about 240 ng/ml from a mean of about 2 to about 4.5 hours after administration, and a mean minimum plasma concentration from about 3 to about 30 ng/ml from a mean of about 10 to about 14 hours after repeated administration every 12 hours through steady-state conditions.

6. The controlled release composition of claim 5, wherein said film coating comprises a water insoluble material selected from the group consisting of shellac or zein, a water insoluble cellulose, or a polymethacrylate.

7. A controlled release tablet for oral administration comprising from about 10 to about 160 mg oxycodone or an oxycodone salt dispersed in a controlled release matrix, said tablet providing an in-vitro dissolution of the dosage form, when measured by the USP Paddle Method at 100 rpm at 900 ml aqueous buffer (pH between 1.6 and 7.2) at 37° C., between 12.5% and 42.5% (by wt) oxycodone released after 1 hour, between 25% and 55% (by wt) oxycodone released after 2 hours, between 45% and 75% (by wt) oxycodone released after 4 hours and between 55% and 85% (by wt) oxycodone released after 6 hours, the in vitro release rate being substantially independent of pH and chosen such that a mean maximum plasma concentration of oxycodone from about 6 to about 240 ng/ml is obtained in vivo from a mean of about 2 to about 4.5 hours after administration of the dosage form, and a mean minimum plasma concentration from about 3 to about 30 ng/ml from a mean of about 10 to about 14 hours after repeated administration every 12 hours through steady-state conditions.

8. A dosage form according to claim 7, wherein the in vitro dissolution rate is between 17.5% and 38% (by wt) oxycodone released after 1 hour, between 30% and 50% (by wt) oxycodone released after 2 hours, between 50% and 70% (by wt) oxycodone released after 4 hours and between 60% and 80% (by wt) oxycodone released after 6 hours.

9. A dosage form according to claim 7, wherein the in vitro dissolution rate is between 17.5% and 32.5% (by wt) oxycodone released after 1 hour, between 35% and 45% (by wt) oxycodone released after 2 hours, between 55% and 65% (by wt) oxycodone released after 4 hours and between 65% and 75% (by wt) oxycodone released after 6 hours.

* * * * *